US012630853B2

(12) United States Patent
Lattemann et al.

(10) Patent No.: US 12,630,853 B2
(45) Date of Patent: May 19, 2026

(54) BIOTECHNOLOGICAL OPTIMIZATION OF MICROORGANISMS FOR THE 1,2-DEHYDROGENATION OF STEROIDS

(71) Applicant: EUROAPI FRANCE, Paris (FR)

(72) Inventors: Claus Tobias Lattemann, Frankfurt (DE); Bernd Janocha, Frankfurt (DE); Hans-Falk Rasser, Frankfurt (DE); Sebastian Rissom, Frankfurt (DE)

(73) Assignee: EUROAPI FRANCE, Paris (FR)

( * ) Notice: Subject to any disclaimer, the term of this patent is extended or adjusted under 35 U.S.C. 154(b) by 937 days.

(21) Appl. No.: 17/429,198

(22) PCT Filed: Feb. 7, 2020

(86) PCT No.: PCT/EP2020/053167

§ 371 (c)(1), (2) Date: Aug. 6, 2021

(87) PCT Pub. No.: WO2020/161317

PCT Pub. Date: Aug. 13, 2020

(65) Prior Publication Data

US 2022/0136029 A1 May 5, 2022

(30) Foreign Application Priority Data

Feb. 8, 2019 (EP) .................................... 19305153

(51) Int. Cl.

| | |
|---|---|
| ***C12P 33/02*** | (2006.01) |
| ***C12N 1/205*** | (2026.01) |
| ***C12N 9/02*** | (2006.01) |
| ***C12N 9/04*** | (2006.01) |
| ***C12N 15/74*** | (2006.01) |
| ***C12R 1/365*** | (2006.01) |

(52) U.S. Cl.

CPC .............. *C12P 33/02* (2013.01); *C12N 1/205* (2021.05); *C12N 9/0006* (2013.01); *C12N 9/001* (2013.01); *C12N 15/74* (2013.01); *C12R 2001/365* (2021.05); *C12Y 101/01053* (2013.01); *C12Y 103/99004* (2013.01)

(58) Field of Classification Search

CPC ....... C12P 33/02; C12N 1/205; C12N 9/0006; C12N 9/001; C12N 15/74; C12R 2001/365; C12R 2001/01; C12Y 101/01053; C12Y 103/99004; C07J 5/0053

See application file for complete search history.

(56) References Cited

U.S. PATENT DOCUMENTS 3,047,469 A 7/1962 Sih et al.

FOREIGN PATENT DOCUMENTS

WO WO 2001/031050 A1 5/2001
WO WO 2006/124141 A2 11/2006

OTHER PUBLICATIONS

Mythen, S. (2018) Characterization of Enzymatic Pathways Involved in Cortisol and Bile Acid Metabolism by the Gut Microbiota, Master's thesis, University of Illinois at Urbana-Champaign. (Year: 2018).*
Xu et al., Strategies used for genetically modifying bacterial genome: site-directed mutagenesis, gene inactivation, and gene over-expression, 2016, J Zhejiang Univ-Sci B (Biomed & Biotechnol) 17(2):83-99 (Year: 2016).*
Pickens et al., Metabolic Engineering for the Production of Natural Products, 2011, Annu Rev Chem Biomol Eng; 2: 211-236, p. 1-29 (Year: 2011).*
AIY18834.1, GenBank database, 2015. (Year: 2015).*
CP009896.1, Genbank database, 2015. (Year: 2015).*
GenBank database, 2015. (Year: 2015).*
Covey et al., "Inactivation of *Streptomyces hydrogenans* 20.beta.-hydroxysteroid dehydrogenase by an enzyme-generated ethoxyacetylenic ketone in the presence of a thiol scavenger", Biochemistry, Nov. 18, 1986, 25(3): 7288-7294.
Ghosh et al., "Three-dimensional structure of holo 3 alpha,20 beta-hydroxysteroid dehydrogenase: a member of a short-chain dehydrogenase family", Proc Natl Acad Sci USA, Nov. 15, 1991, 88(22): 10064-10068.
European Search Report for European Patent Application No. 19305153.9, dated Jun. 18, 2019, 7 pages.
International Search Report and Written Opinion for PCT International Patent Application No. PCT/EP2020/053167, dated Mar. 12, 2020, 7 pages.
Chen et al., "Enzymic reduction of prednisolone to 20β-hydroxyprednisone with Arthrobacter simplex", Enzyme Microb Technol., Feb. 1989, 11(2): 116-120.
Zhang et al., "Construction of engineered Arthrobacter simplex with improved performance for cortisone acetate biotransformation", Appl Mircrobiol Biotechnol., Nov. 2013, 97(21): 9503-9514, ePublished Sep. 14, 2013.
Shtratnikova et al., "Complete Genome Sequence of Steroid-Transforming Nocardioides simplex VKM Ac-2033D," Genome Announcements, Jan./Feb. 2015, 3(1): e01406-14.
NIH, National Library of Medicine, GenBank Accession No. AIY17335.1, "3-alpha-(or 20-beta)-hydroxysteroid dehydrogenase fabG3 [Pimelobacter simplex]", Jan. 27, 2020.
NIH, National Library of Medicine, GenBank Accession No. AIY17521.1, "3-alpha-(or 20-beta)-hydroxysteroid dehydrogenase [Pimelobacter simplex]", Jan. 27, 2020.
NIH, National Library of Medicine, GenBank Accession No. AIY18834.1, "20-beta-hydroxysteroid dehydrogenase [Pimelobacter simplex]", Jan. 27, 2020.
NIH, National Library of Medicine, GenBank Accession No. AIY20132.2, "20-beta-hydroxysteroid dehydrogenase FabG3 [Pimelobacter simplex]", Jan. 27, 2020.
NIH, National Library of Medicine, GenBank Accession No. AIY19232.1, "3-alpha-(or 20-beta)-hydroxysteroid dehydrogenase [Pimelobacter simplex]", Jan. 27, 2020.

(Continued)

*Primary Examiner* — Robert B Mondesi
*Assistant Examiner* — Naghmeh Nina Moazzami

(57) ABSTRACT

The present invention concerns a genetically modified bacterium and to its industrial application, in particular in the 1,2-dehydrogenation of steroids.

20 Claims, 3 Drawing Sheets

Figure 1:
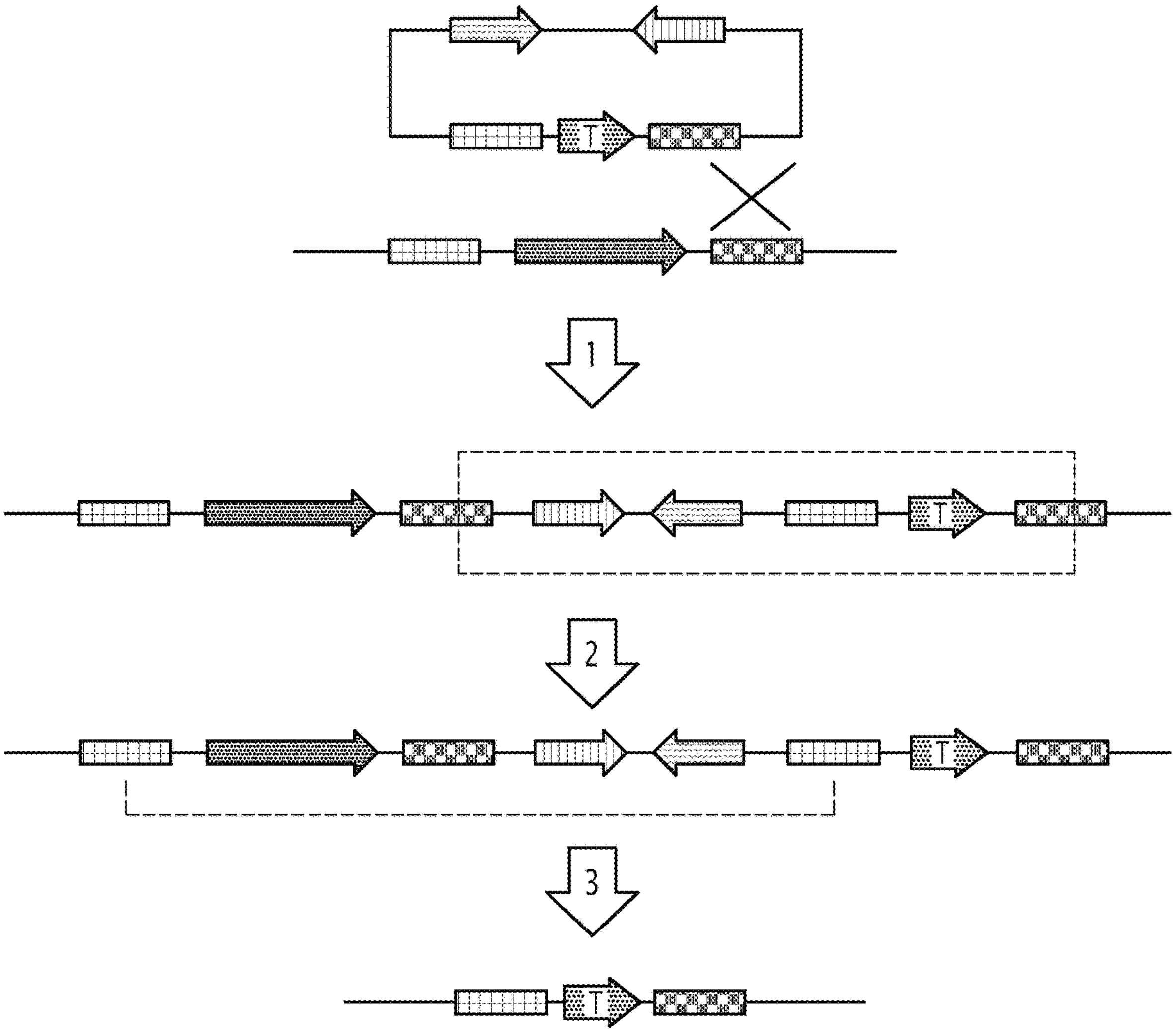

Specification includes a Sequence Listing.

(56) References Cited

OTHER PUBLICATIONS

NIH, National Library of Medicine, GenBank Accession No. AIY19504.1, "20-beta-hydroxysteroid dehydrogenase [Pimelobacter simplex]", Jan. 27, 2020.
NIH, National Library of Medicine, GenBank Accession No. AIY15724.2, "3-ketosteroid-delta-1-dehydrogenase kstD3 [Pimelobacter simplex]", Jan. 27, 2020.
NIH, National Library of Medicine, GenBank Accession No. AIY15933.1, "3-ketosteroid-delta-1-dehydrogenase kstD1 [Pimelobacter simplex]", Jan. 27, 2020.
NIH, National Library of Medicine, GenBank Accession No. AIY17665.3, "3-ketosteroid-delta-1-dehydrogenase KstD3 [Pimelobacter simplex]", Jan. 27, 2020.
NIH, National Library of Medicine, GenBank Accession No. AIY19527.1, "3-ketosteroid-delta1-dehydrogenase kstD1 [Pimelobacter simplex]", Jan. 27, 2020.
NIH, National Library of Medicine, GenBank Accession No. AIY19529.1, "3-ketosteroid-delta-1-dehydrogenase KstD2 [Pimelobacter simplex]", Jan. 27, 2020.

* cited by examiner

SEQUENCE LISTING

<160> NUMBER OF SEQ ID NOS: 3

<210> SEQ ID NO 1
<211> LENGTH: 748
<212> TYPE: DNA
<213> ORGANISM: Nocardioides simplex -continued

<400> SEQUENCE: 1

```
ggtcgtcctc gtcaccggag gcgcccgcgg gctgggcgcc gccttcgccc gcggcatcgt      60

cgccgccggc ggccgggtcg tcatcggcga cctgctggac gacgagggcg ccgccgtcgc     120

cgacgagctc ggcgccgcgg cccgctacgt ccacctcgac gtcaccagcg aggagtcctg     180

ggaggccgcc gtcgccgcga gcgtcgacgc cttcggccgg ctcgacgggc tggtcaacaa     240

cgccggcatc tcggccaccg gccagctgac cgccgacgag ccgaccgacg tcttccgccg     300

gatcatcgag atcaacctga tcgccgtcca caccgggctg cgcgccgtcg tccccgcgat     360

gcggacggcg ggcggcggct cgatcgtcaa catctcgtcg gccgcgggcc tgatgggcat     420

ggcgatgacc agcggctacg gcgccgccaa gtggggcgtg cgcgggctca gcaagatcgc     480

ggcggtcgag ctcggtcgcg accggatccg ggtcaactcg gtgcaccccg gcatggtcct     540

gacgccgatg accgccccga ccgggatcgt cgccgacgag ggcgccttcc cgaacaaccc     600

gtaccagcgg gtcggccggc ccgaggagct cgtgggtgcg gtcgtccacc tgctgagcga     660

cgccgcgtcg tacacgaccg gcgccgagct cgccgtcgac ggcggctgga ccgccggtcc     720

gtcggtggag tacatcgcag gtcggtga                                      748
```

<210> SEQ ID NO 2
<211> LENGTH: 825
<212> TYPE: DNA
<213> ORGANISM: Nocardioides simplex

<400> SEQUENCE: 2

```
gtgccgctgg ccggcaccct gcccgcgcgc ccgcgcggac ggcgcttcat tggggccatg      60

acccagatcc aggccccgac gaacccgtcc accactcccg gccgcgtcgc cgaccgcgtc     120

gtcatcgtga cgggaggagc ccgcggcatc ggcgccgcct gcgtgcgcgc actcgtcgcc     180

gagggcgccc gggtggtggt cgccgacgtc ctcgaggccg aggcgagcgc cctcgtcgcc     240

gcgctggggg agcggacggc gtacgtcccg ctcgacgtga cgagcgagga ggcgtggcag     300

cacgcggtcg cggcggccga ggagcgcttc gggccggtct cgggactcgt caacaacgcc     360

ggcatcgtgc acatcgaccc gatcgagacc ctgagcgagg ccgactaccg gcgggtgatc     420

gacgtcaacc aggtcggcgt cttcctcggc atgaaggcgg tcatcgggtc gatgcggcgc     480

gcggggggcg gctcgatcgt caacatctcc tcgaccggcg ggctggtcgc ctactcccgg     540

atcctcgggt acgtcgcctc gaagtgggcc gtgcgcggca tgaccaagac cgccgcgcag     600

gagctcggcc ccgacggcat ccgggtcaac tcggtgcacc ccggcatcgt cgcctccgcg     660

atgaccgcga gctccgaccg ctcccacgag caggtcagga cccagccgct ggcgcgggcg     720

gcggacccgt ccgagatcgg cgcgctcgtg ctcttcctga tctcggagga gtccagctac     780

agcaccggct cggagttcgt cgccgacggg ggcttcacct cgctc                   825
```

<210> SEQ ID NO 3
<211> LENGTH: 741
<212> TYPE: DNA
<213> ORGANISM: Mycobacterium avium

<400> SEQUENCE: 3

```
gtgggacggg tagacggcaa ggttgcgctg atcagcgggg gcgcccgcgg catgggcgcc      60

gagcacgcgc ggctgctggc ggccgagggc gccaaggtgg tgatcggcga catcctcgac     120

gacgagggca aggccgtggc cgacgagatc ggcgactcgg tgcgctacgt ccacctggac     180
```

-continued

```
gtcacccagc ccgaccagtg ggacgccgcc gtcgaaaccg ccgtcggcga attcggcaag    240

ctcaacgtgt tggtcaacaa cgccggcacc gtcgcgctcg ggccgctgaa gagcttcgat    300

ctggccaagt ggcagaaggt gattgacgtc aacctgaccg gcaccttcct gggcatgcgg    360

gtggccgtcg agccgatgat cgcggccggc ggcggctcga tcatcaacat ctcctccatc    420

gaggggctgc gcggtgcgcc catggtgcac ccctacgtcg cctccaagtg gggcgtgcgc    480

ggcctggcga agtccgcggc gctggagctg gcgccgcaca acatccgggt caactccgtg    540

caccccggct tcatccgcac cccgatgacc aaacacctgc ccgacgacat ggtgaccgtc    600

ccgctcggcc gtccggccga gtcccgcgag gtgtcgacgt tcgtcttgtt cctggccagc    660

gacgagtcgt cgtacgcgac cggcagcgaa ttcgtgatgg acggcggact ggtcaccgac    720

gtgccgcaca agcagttcta g                                               741
```

BIOTECHNOLOGICAL OPTIMIZATION OF MICROORGANISMS FOR THE 1,2-DEHYDROGENATION OF STEROIDS

RELATED APPLICATIONS

This application is a 35 U.S.C. § 371 filing of International Patent Application No. PCT/EP2020/053167, filed Feb. 7, 2020, which claims priority to European Patent Application No. 19305153.9, filed Feb. 8, 2019, the entire disclosures of which are hereby incorporated herein by reference.

The present invention concerns a genetically modified bacterium and its industrial application, in particular in the 1,2-dehydrogenation of steroids.

The 1,2-dehydrogenation of steroids (also named Δ1-dehydrogenation) can be carried out by a biotransformation with a bacterium having the appropriate enzyme system. For example the conversion can be catalyzed by a microorganism of the Nocardioidaceae family, which is prepared and used as a bacterial suspension or as a supernatant after cell-lysis of the bacterial suspension. Unfortunately the microorganism also expresses an enzyme that catalyses a second (unwanted) reaction on the steroid molecule, which is a reduction of the keto-group at position 20 and leads to the production of side products called here “20-OH impurities”. These two reactions are schematized hereafter with the example of hydrocortisone.

Primary reaction by Δ1-dehydrogenase

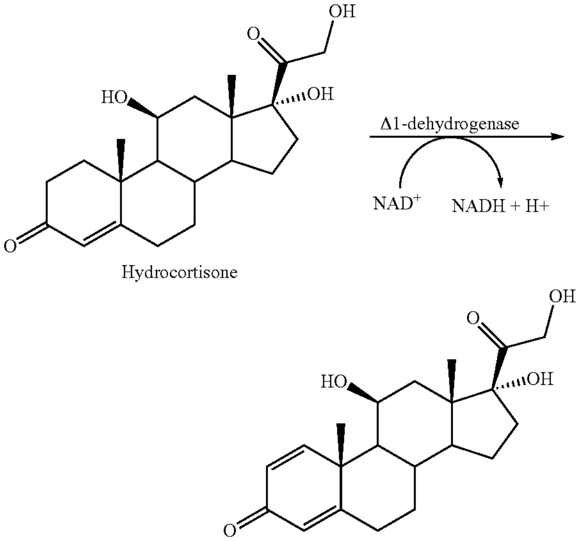

Hydrocortisone

Deltahydrocortisone
Prednisolone

Seconadry reaction by 20-β-dehydrogenase

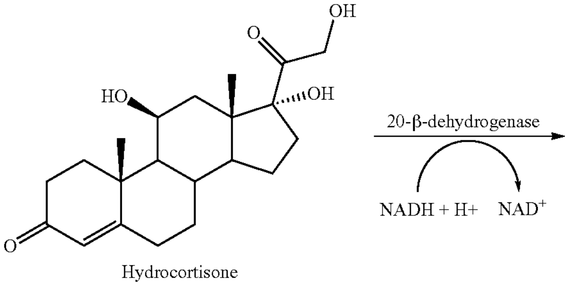

Hydrocortisone

-continued

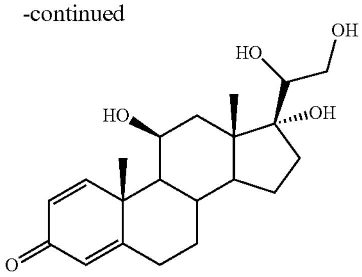

20-β-OH-Deltahydrocortisone

The enzyme 20β-HSDH (20-beta-hydroxysteroid dehydrogenase), which leads to a keto-reduction in steroids at position 20, has been identified to be responsible for this side reaction.

The inventors have now identified the gene responsible for the side reaction activity and genetically engineered a microorganism devoid of this activity. When used in steroid conversions, it does not produce the unwanted side-product any longer and said genetically engineered microorganism according to the invention can be directly used in steroid conversions without any potential maturation step(s). Additional steps for purification of the product to remove the unwanted side product can also be omitted. The product of the biotransformation can be used directly after production. In conclusion this leads to a higher product yield, higher product quality and simpler production process.

DESCRIPTION OF THE INVENTION

A first aspect of the invention thus relates to a genetically modified bacterium wherein expression of a gene coding a 20β-HSDH is reduced or suppressed compared to a corresponding unmodified bacterium, wherein the corresponding unmodified bacterium has Δ1-dehydrogenase activity and 20-β-dehydrogenase activity.

As used herein, the term “a corresponding unmodified bacterium” denote the same strain of bacterium as the unmodified bacterium which is then submitted to genetic modification.

The term “bacterium” means a prokaryotic microorganism. The unmodified bacterium has 20β-HSDH activity and Δ1-dehydrogenase activity. In one embodiment, the bacterium is from an order chosen among the Actinomycetales order, the Clostridiales order, the Aeromonadales order, the Pasteurellales order, the Bacillales order, the Lactobacillales order, the Bifidobacteriales order and the Coriobacteriales order. In one preferred embodiment, the bacterium is from the Actinomycetales order. For example the bacterium can be a Nocardiodiaceae such as *Nocardioides simplex*, a Streptomycetaceae such as *Streptomyces albus* or a Mycobacteriaceae, such as *Mycobacterium avium* and in particular *Mycobacterium avium* subsp. paratuberculosis MAP4. In a particular embodiment, the bacterium is from the family Nocardioidaceae, preferably *Nocardioides* and most preferably the bacterium is *Nocardioides simplex*.

The term “bacterium from the family Nocardioidaceae” means any bacterium from this family having a 20β-HSDH activity and Δ1-dehydrogenase activity, such as, for example a bacterium of the genus *Actinopolymorpha, Aeromicrobium, Flindersiella, Friedmanniella, Kribbella, Marmoricola, Micropruina, Mumia, Nocardioides, Pimelobacter, Propionicicella, Propionicimonas, Tenggerimyces*, or *Thermasporomyces*. Preferably the bacterium from family Nocardioidaceae is *Nocardioides simplex* (previously named *Arthrobacter simplex* or *Corynebacterium simplex* or *Pimelobacter simplex*). Preferably the bacterium is *Nocardioides simplex* ATCC6946. Other preferred bacteria include *Friedmanniella flava* (Taxonomy ID:1036181), *Friedmanniella sagamiharensis* (Taxonomy ID:546874), *Nocardioides dokdonensis* FR1436 (Taxonomy ID:1300347), *Nocardioides lianchengensis* (Taxonomy ID:1045774), *Nocardioides psychrotolerans* (Taxonomy ID:1005945), *Nocardioides szechwanensis* (Taxonomy ID:1005944), *Corynebacterium coyleae* (Taxonomy ID:53374), *Corynebacterium glyciniphilum* AJ 3170 (Taxonomy ID:1404245), *Corynebacterium kroppenstedtii* DSM 44385 (Taxonomy ID:645127), *Corynebacterium lowii* (Taxonomy ID:1544413), *Corynebacterium spheniscorum* (Taxonomy ID:185761), *Corynebacterium vitaeruminis* DSM 20294 (Taxonomy ID:1224164), *Aeromicrobium marinum* DSM 15272 (Taxonomy ID:585531), *Nocardioides luteus* (Taxonomy ID:1844), *Corynebacterium halotolerans* YIM 70093=DSM 44683 (Taxonomy ID:1121362), *Corynebacterium maris* DSM 45190 (Taxonomy ID:1224163), *Corynebacterium riegelii* (Taxonomy ID:156976).

The term "gene" means a DNA sequence that codes for, or corresponds to, a particular sequence of amino acids which comprise all or part of one or more proteins or enzymes, and may or may not include regulatory DNA sequences, such as promoter sequences, which determine for example the conditions under which the gene is expressed. In particular, the term gene may be intended for the genomic sequence encoding a protein, i.e. a sequence comprising regulator, promoter, intron and exon sequences.

As used herein, terms "gene coding a 20β-HSDH" correspond to a gene coding a 20β-HSDH of any bacterium. Preferably the gene coding a 20β-HSDH has at least 60% identity with sequence SEQ ID NO: 1, more preferably it has more than 70%, 75%, 80%, 85%, 90%, 95%, and most preferably more than 99% of identity with sequence SEQ ID NO: 1. According to an embodiment, the gene coding a 20β-HSDH have at least 60% of identity with sequence SEQ ID NO: 3, more preferably it has more than 70%, 75%, 80%, 85%, 90%, 95%, and most preferably more than 99% of identity with sequence SEQ ID NO: 3.

By "gene having at least x % identity with a reference sequence", it is intended that the sequence of the nucleic acid differs from the reference sequence by up to 100-x nucleotide alterations per each 100 nucleotides of the reference sequence over its whole length. In other words, to obtain a nucleic acid having a sequence at least x % identity with a reference sequence, up to 100-x % of the nucleotides in the subject sequence may be inserted, deleted or substituted with another amino acid or nucleotide.

A nucleic acid sequence "at least 60%, 70%, 75%, 80%, 85%, 90%, 95% or 99% identical" to a reference sequence may comprise mutation(s), such as deletion(s), insertion(s) and/or substitution(s) compared to the reference sequence. In case of substitution, the substitution preferably corresponds to a silent substitution or a substitution leading to a conservative substitution in the translated amino acid sequence.

Methods for comparing the identity of two or more sequences are well known in the scientific community. For instance, programs available in the Wisconsin Sequence Analysis Package, version 9.1, for example the programs BESTFIT and GAP, may be used to determine the identity percentage between two sequences. BESTFIT uses the "local homology" algorithm of Smith and Waterman and finds the best single region of similarity between two sequences. Other programs for determining identity between sequences are also known in the art, for instance the Needle program, which is based on the Needleman and Wunsch algorithm, described in Needleman and Wunsch (1970) J. Mol Biol. 48:443-453, with for example the following parameters for polynucleotide sequence comparison: comparison matrix: DNAFULL; gap open penalty=10, gap extend penalty=0.5, end gap penalty: false, end gap open penalty=10, end gap extend penalty=0.5.

The term "genetically modified" means any detectable change in genetic material, e.g. DNA, RNA, cDNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. Generally a mutation is identified in a subject by comparing the sequence of a nucleic acid or polypeptide expressed by said subject with the corresponding nucleic acid or polypeptide expressed in a control population.

Terms "expression of a gene coding a 20β-HSDH is reduced or suppressed" means reduction or suppression of the expression level of messenger RNA (mRNA) and/or of the protein encoded by the gene coding a 20β-HSDH. The expression of a gene coding a 20β-HSDH can be reduced by at least 75%, 80%, 85%, 90% or 95% compared to the unmodified bacterium. Preferably the expression of a gene coding a 20β-HSDH is reduced by 100%, thus corresponding to the suppression of the expression.

Level of expression of a gene or a nucleic acid can be measured by methods which are well known to the person skilled in the art, including in particular direct hybridization based assays and amplification-based assays.

The expression of a gene coding a 20β-HSDH can be reduced or suppressed compared to the unmodified bacterium by inactivation or deletion of this gene. In a particular embodiment the gene coding a 20β-HSDH is mutated, and preferably truncated.

Preferably the genetically modified bacterium does not comprise any exogenous DNA.

Laboratory methods for inactivation, deletion or truncation of a gene are well known in the art.

As intended herein, when the gene coding a 20β-HSDH is mutated and/or truncated it may not encode a fully functional 20β-HSDH protein, but encodes a 20β-HSDH protein having an activity lower than that of the corresponding natural 20β-HSDH protein measured in the same conditions, in particular the encoded 20β-HSDH protein may have no activity.

The genetically modified bacterium according to the invention preferably has Δ1-dehydrogenase activity, but has reduced or is devoid of 20-β-dehydrogenase activity compared to the unmodified bacterium.

Thus, as readily apparent in this application, the invention relates to a genetically modified bacterium wherein:

- the corresponding unmodified bacterium has Δ1-dehydrogenase activity and 20-β-dehydrogenase activity,
- at least one genetically modification induces a reduced or suppressed expression of a gene coding a 20-beta-hydroxysteroid dehydrogenase (20β-HSDH), and
- preferably said genetically modified bacterium keep its Δ1-dehydrogenase activity.

Preferably, the genetically modified bacterium according the invention has Δ1-dehydrogenase activity, but due to genetic modification has reduced or is devoid of 20-β-dehydrogenase activity compared to the unmodified bacterium.

A second aspect of the invention relates to a method for production of a genetically modified bacterium according to the invention comprising:

a) providing a bacterium which has Δ1-dehydrogenase activity and 20-β-dehydrogenase activity; and b) inactivating or deleting the gene coding a 20β-HSDH.

Step b of the method for production of a genetically modified bacterium according to the invention can consist on the mutation, the truncation or deletion of the gene coding a 20β-HSDH. Mutation or truncation may be realized by any methods known to the skilled in the art, and preferably by double crossover of the gene coding the 20β-HSDH.

Preferably the obtained genetically modified bacterium does not comprise any exogenous DNA.

In another aspect, the invention relates to a method for the production 1,2-dehydrogenated steroid comprising:

a) providing a steroid which is not 1,2-dehydrogenated;

b) contacting said steroid which is not 1,2-dehydrogenated with a bacterium according to the invention or an extract thereof under conditions sufficient to obtain 1,2-dehydrogenated steroid.

Preferably the steroid which is not 1,2-dehydrogenated used in the method for the production 1,2-dehydrogenated steroid according to the invention is a corticosteroid.

In a particular embodiment the steroid which is not 1,2-dehydrogenated used in the method is progesterone, testosterone, androstenedione or a derivative of these molecules, which contain a steroid-scaffold containing a ring A of six carbon atoms not dehydrogenated between at positions 1,2.

In a particular embodiment, the steroid which is not 1,2-dehydrogenated is:

11 beta 17,21-trihydroxypregn-4-ene-3,20-dione (hydrocortisone) and said method is for the production of 11beta,17alpha,21-trihydroxy-1,4-pregnadiene-3,20-dione (prednisolone); or 17alpha,21-dihydroxy-4-pregnene-3,11,20-trione (cortisone) and said method is for the production of 17alpha, 21-dihydroxy-1,4 pregnadiene-3,11,20-trione (prednisone); or Pregn-4-ene-3,20-dione and said method is for the production of Pregna-1,4-diene-3,20-dione; or 11beta,17,21-Trihydroxy-6alpha-1,4-pregnene-3,20-dione (6-methylhydrocortisone) for the production of 11 beta,17alpha,21-trihydroxy-6alpha-methyl-1,4-pregnadiene-3,20-dione (6-methylprednisolone); or 9,11-dehydrocortexolone and said method is for the production of 1,2-9,11-dehydrocortexolone; or 9,11 dehydrocortexolone-17,21-diacetate and said method is for the production of 1,2-9,11 dehydrocortexolone; or 9,11-16,17-dehydrocortexolone-21-acetate and said method is for the production of 1,2-9,11-16,17-dehydrocortexolone-21-acetate; or 16-alpha-methylhydrocortisone and said method is for the production of 16-alpha-methylprednisolone.

In an embodiment, step b) of the method for the production 1,2-dehydrogenated steroid is done with an extract of a bacterium according to the invention. Said extract, preferentially has Δ1-dehydrogenase activity, and preferentially has reduced or is devoid of 20-β-dehydrogenase activity. In particular such extract can be obtained by cell-lysis of the bacterium according to the invention and optionally fractionation of the cell-lysis product in order to concentrate the Δ1-dehydrogenase activity or to facilitate purification of the Δ1-dehydrogenase activity.

The method for the production 1,2-dehydrogenated steroid can further comprises recovering and purifying said 1,2-dehydrogenated steroid.

Preferably the method for the production 1,2-dehydrogenated steroid does not comprise a step of elimination of 20β-dehydrogenated steroid. Indeed this step can be unnecessary if the expression of a gene coding a 20β-HSDH is significantly reduced.

Further the method for the production 1,2-dehydrogenated steroid may comprises formulating the 1,2-dehydrogenated steroid into a pharmaceutical composition.

In another aspect, the invention relates to the use of a bacterium or an extract thereof according to the invention for the production 1,2-dehydrogenated steroid from steroid which is not 1,2-dehydrogenated.

Said extract, preferentially has Δ1-dehydrogenase activity, and preferentially has reduced or is devoid of 20-β-dehydrogenase activity. In particular such extract can be obtained by cell-lysis of the bacterium according to the invention and optionally after fractionation of the cell-lysis product in order to concentrate the Δ1-dehydrogenase activity or to facilitate purification of the Δ1-dehydrogenase activity.

Preferably the steroid which is not 1,2-dehydrogenated is a corticosteroid.

In a particular embodiment, the steroid which is not 1,2-dehydrogenated is progesterone, testosterone, androstenedione or a derivative of these molecules, which contain a steroid-scaffold containing a ring A of six carbon atoms not dehydrogenated between at positions 1,2.

In a particular embodiment, the steroid which is not 1,2-dehydrogenated is:

11 beta 17,21-trihydroxypregn-4-ene-3,20-dione (hydrocortisone) and 11beta,17alpha,21-trihydroxy-1,4-pregnadiene-3,20-dione (prednisolone) is produced; or 17alpha,21-dihydroxy-4-pregnene-3,11,20-trione (cortisone) and 17alpha,21-dihydroxy-1,4 pregnadiene-3,11, 20-trione (prednisone) is produced; or Pregn-4-ene-3,20-dione and Pregna-1,4-diene-3,20-dione is produced; or 11beta,17,21-Trihydroxy-6alpha-1,4-pregnene-3,20-dione (6-methylhydrocortisone) and 11beta,17alpha, 21-trihydroxy-6alpha-methyl-1,4-pregnadiene-3,20-dione (6-methylprednisolone) is produced; or 9,11-dehydrocortexolone and 1,2-9,11-dehydrocortexolone is produced; or 9,11 dehydrocortexolone-17,21-diacetate and 1,2-9,11 dehydrocortexolone is produced; or 9,11-16,17-dehydrocortexolone-21-acetate and 1,2-9, 11-16,17-dehydrocortexolone-21-acetate is produced; or 16-alpha-methylhydrocortisone and 16-alpha-methylprednisolone is produced.

As used herein, the term "pharmaceutical composition" refers to a preparation of 1,2-dehydrogenated steroid with other chemical components such as physiologically suitable carriers and excipients. The purpose of a pharmaceutical composition is to facilitate administration of said 1,2-dehydrogenated steroid to an organism.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Typically, a pharmaceutical composition may comprise the 1,2-dehydrogenated steroid of the invention and a pharmaceutical acceptable vehicle.

The invention will be further illustrated by the following figures and examples.

FIGURES

FIG. 1: Schematic representation of gene inactivation by double-crossover. Plasmid with truncated form of the gene of interest (arrow comprising the letter "T") flanked by two homologous shoulders (boxes comprising squares) and genes of apramycin resistance and β-glucuronidase (arrows comprising vertical lines and wavy lines) comes into contact with the chromosome of the bacterium and one of the homologous shoulders recombines with respective sequence in the chromosome (step 1). This step results in forming of intermediate single crossover construction, the whole plasmid is integrated into the genome (encircled by dot line). Then the strain contains two variants of the gene of interest and exhibits resistance to apramycin and β-glucuronidase activity. After several rounds of cultivation (step 2), the two remaining homologous shoulders interact with each other (dotted line) and a double crossover occurs (step 3). Then the obtained strain contains only the truncated form of the gene (arrow comprising the letter "T").

Figure 2:
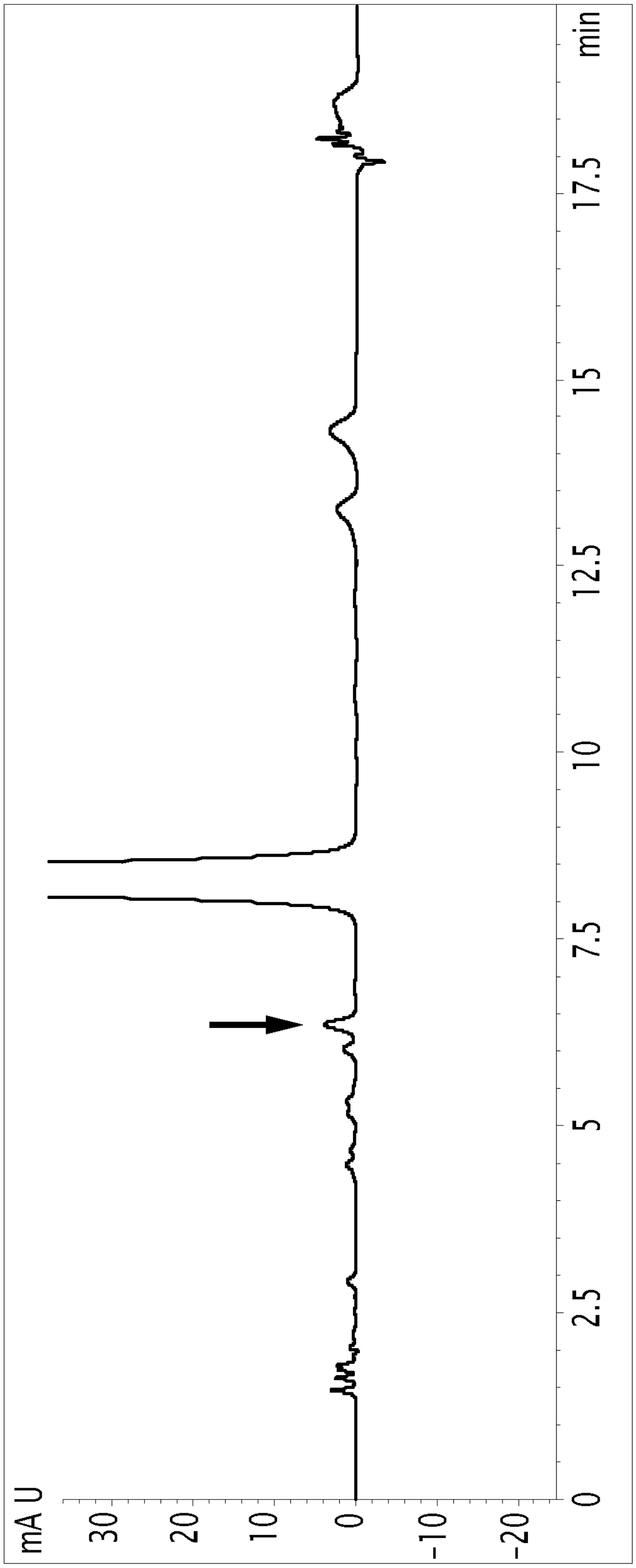

FIG. 2: HPLC-chromatogram of the obtained product after a classical process for production of prednisolone from hydrocortisone with *N. simplex*. The arrow points to 20-OH Prednisolone impurities.

Figure 3:
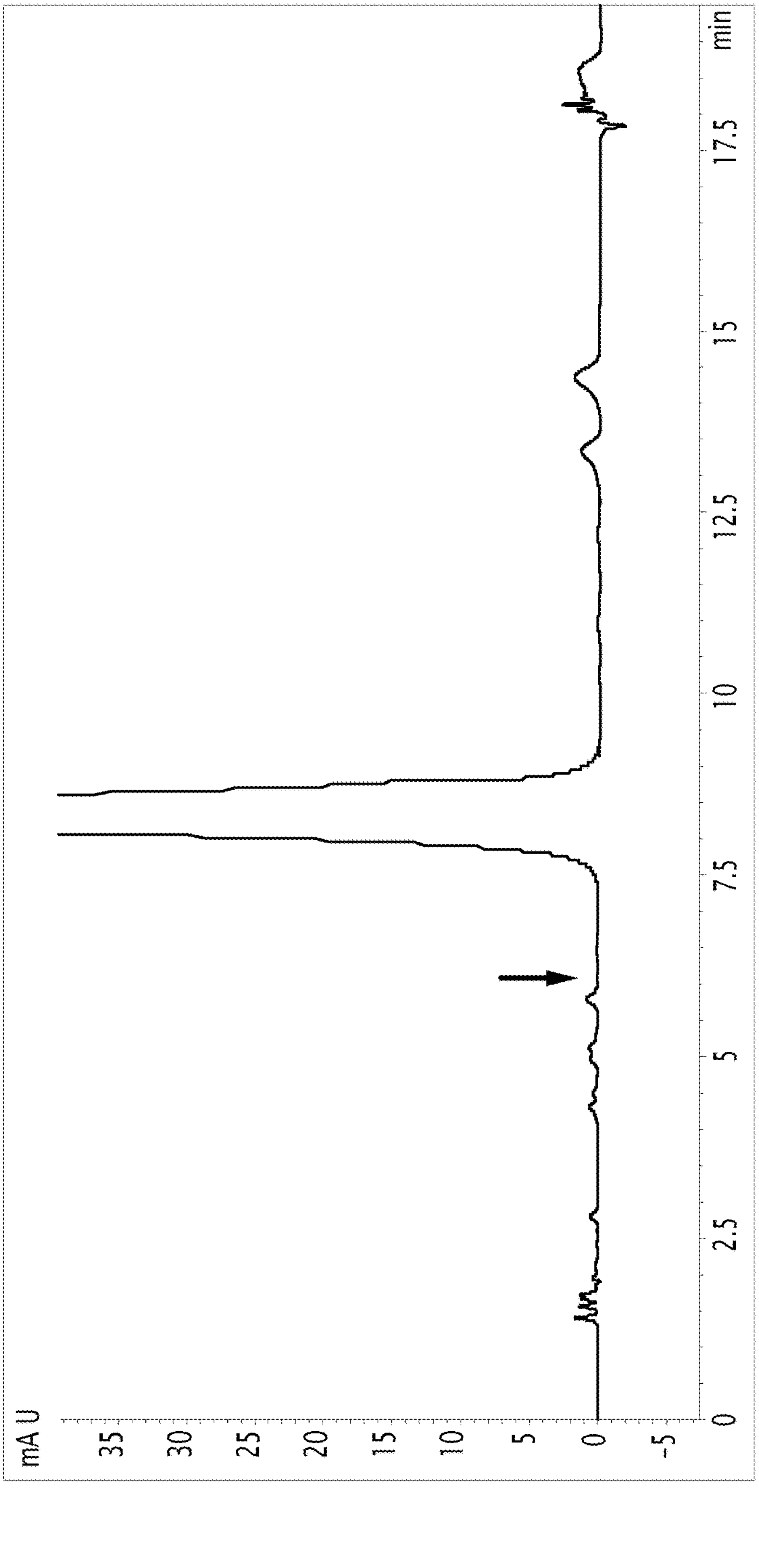

FIG. 3: HPLC-chromatogram of the obtained product after a classical process for production of prednisolone from hydrocortisone with double cross-over mutants NOSIM5169 of *N. simplex*. The arrow points to the location wherein 20-OH Prednisolone impurities are normally observed.

SEQUENCE LISTING

SEQ ID NO: 1 corresponds to the sequence of NOSIM5169 of *N. simplex*.

SEQ ID NO: 2 corresponds to the sequence of NOSIM3735 of *N. simplex*.

SEQ ID NO: 3 corresponds to the sequence of the gene of the 20β-HSDH of *Mycobacterium avium* subsp. paratuberculosis MAP4.

Example

Analyzing the genome of *N. simplex*, two possible genes for the 20β-HSDH were found, called NOSIM5169 (corresponding to sequence SEQ ID NO: 1) and NOSIM3735 (corresponding to sequence SEQ ID NO: 2). They both share similarities with the sequence of the gene responsible for the 20β-HSDH of *Mycobacterium avium* subsp. paratuberculosis MAP4 (corresponding to sequence SEQ ID NO: 3).

1. Plasmid Construction (NOSIM5169)

Plasmids for inactivation of NOSIM5169 were constructed as follows: The homologous shoulders of 2.0 and 1.7 kbp sizes were amplified by PCR. The primers used for amplification of one shoulder contained XbaI and EcoRV restriction sites and primers for the second homologous shoulder were designed to contain EcoRV and EcoRI restriction sites.

The shoulders were subsequently cloned into a first plasmid.

To obtain the new second plasmid the gene for hygromycin resistance was blunt-end cloned into EcoRV restriction site.

A plasmid without the hygromycin resistance gene was named "second plasmid -hyg".

2. Electroporation Protocol for *N. simplex*

The protocol is based on the procedure described for *Arthrobacter* (Zhang et al., 2011). The optimized procedure for the preparation of electrocompetent cells was as follows: The cells of *N. simplex* were inoculated into 20 ml of LB+Ph (LB stands for lysogeny broth, and Ph stands for Phosphomycin) and cultivated until stationary phase was reached. Then 1% inoculum from the preculture was inoculated into fresh LB medium and cultivated until optical density approached 0.4-0.5 at 600 nm. Then ampicillin (Ap) and glycine were added to a final concentration of 30 μg/l and 5 g/l, respectively, and the cultivation was continued. After 3 h the cultures were placed on ice and harvested by centrifugation (4500 rpm, 6 min, 4° C.). Following three washes in ice-cold electroporation buffer (0.5 M sorbitol, 10% glycerol), the cells were concentrated 100-fold by centrifugation. Finally, the suspension was distributed into 60 μl aliquots and stored on ice (this protocol was used for the generation of *N. simplex* NOSIM5169-hyg).

Alternatively, the protocol for *S. albus* ATCC 21838 (Izumikawa et al., 2003) can be applied. In this case the procedure for the preparation of electrocompetent cells was modified to fit *N. simplex* physiology: 1% inoculum from a stationary phase preculture of *N. simplex* was inoculated into fresh LB+Ph medium and cultivated. When the optical density approached 0.4-0.5 at 600 nm, the cultures were harvested by centrifugation (4500 rpm, 6 min, 4° C.) and washed three times with sterile ice-cold water. Then the mycelium was suspended in 25 ml of cold electroporation buffer (10% sucrose, 15% glycerol) and supplemented with lysozyme (0.5 mg/ml). After 20-min incubation at 37° C. cells were collected by centrifugation and concentrated 100-fold in the electroporation buffer. Finally, the suspension was distributed into 60 μl aliquots and stored on ice.

The optimized electroporation procedure in both cases was as follows: The electro-competent cells were mixed with 500 ng of DNA (prepared from *E. coli* GB2005) and the mixture was transferred into a prechilled electroporation cuvette (0.1 cm electrode). The mixture was subjected to a single pulse using a Eppendorf Pulser with 2.1 kV/cm. Immediately after the electric pulse, cell suspensions were transferred into an Eppendorf tube containing 800 μl of room temperatured recovery medium (SOC) and were incubated with shaking at 850 rpm for 12 h at 30° C. For selection of transformed cells, serial dilutions of bacteria were spread on LB agar plates containing apramycin (Am). With each set of experiment, negative controls were performed by omitting the addition of plasmid DNA.

3. Single Cross-Over Mutants (NOSIM5169)

After electroporation of the strain *N. simplex* with the second plasmid, the single crossover transformant was obtained and patched on LB+Am+X-Gluc agar plates (see FIG. 1 for schematic representation) (X-Gluc stands for monohydrat, X-GlcA). The ability to grow on apramycin and to perform β-glucuronidase (GUS) (e.g. Myronovskyi et al., 2011) reaction confirmed that the transformant was a single crossover mutant. After this the mutant was inoculated in 100 ml of LB+Ph medium and was incubated for 48 h at 28° C., 200 rpm.

4. Double Cross-Over Mutants (NOSIM5169)

Then 1 ml of the culture was transferred into fresh LB+Ph medium and was incubated for another 48 h at the same conditions. This step was repeated several times. After last incubation the serial dilutions of mutants on LB+X-Gluc agar plates were made.

The mutants that did not exhibit GUS-activity were transferred on new LB+X-Gluc and checked once again. Absence of the GUS-activity meant that in those mutants the double cross-over occurred and they have lost the plasmid backbone.

The mutants that passed the second test were grown in LB, their gDNA was isolated and then analyzed by PCR using primers homologous to chromosomal DNA of *N. simplex*.

5. Double Cross-Over Mutants without Foreign DNA (NOSIM5169)

Instead of the second plasmid the "second plasmid -hyg" was used to perform the transformation. The presence of the antibiotic resistance gene (hygromycin resistance) may facilitate further identification of double crossover mutants. However, this resistance gene happened to be inactive in the genome of *N. simplex*.

Thus, after double crossover the obtained mutant is supposed not to contain any exogenous DNA and will be available for further industrial application (FIG. 1).

After introduction of "second plasmid -hyg" into *N. simplex* an apramycin resistant colony was obtained.

This mutant was passed through six cultivations in LB+Ph medium and then serial dilutions of the culture on LB+X-Gluc were made.

Obtained colonies that were unable to grow on apramycin and had no GUS-activity were exposed to further analysis by PCR. The amplification was performed by using two primers homologous to regions of gDNA of *N. simplex* adjacent to NOSIM5169.

6. Inactivation of NOSIM3735

For the construction of strains with inactivated NOSIM3735 the previously described methods could not be applied as the DNA region upstream to the NOSIM3735 was inaccessible for its amplification by PCR. To overcome this challenge a cosmid library containing fragments of the *N. simplex* genome was ordered and sequenced.

To inactivate NOSIM3735, an appropriate cosmid from the cosmid library containing the gene was identified (Sanger sequencing of approx. 1500 cosmids by GATC Biotech, Konstanz) and the gene was replaced by chloramphenicol (Cm) resistance gene, cat, using A-mediated recombination in *E. coli* (e.g. Murphy, 1998). The modified cosmid was than digested by BamHI endonuclease. In this way a mixture of fragments was obtained and among them a fragment that contained the cat-gene instead of NOSIM3735 flanked by two 3-kb shoulders for homologous recombination with *N. simplex* genome. The fragments were separated by agarose gel electrophoresis and the 7-8 kb-fraction was purified and ligated into a BamHI-linearized plasmid. In order to select the mutants that contained the construct with the cat-gene LB+Am+Cm was used as growth medium. Obtained mutants were analyzed by PCR and sequencing. One of the obtained plasmids was further used for inactivation of the NOSIM3735.

The inactivation was carried out according to the protocol previously adapted for inactivation of NOSIM5169 (see point 2 and following).

This mutant was passed through several cultivations in LB+Ph medium and then serial dilutions of the culture on LB+X-Gluc were made.

Obtained colonies that were unable to grow on apramycin and had no GUS-activity were exposed to further analysis by PCR. The amplification was performed by using two primers homologous to regions of gDNA of *N. simplex* adjacent to NOSIM3735.

7. Use of NOSIM3735 and NOSIM5169 on Hydrocortisone

Clones are used in a classical process for production of prednisolone from hydrocortisone.

In brief, hydrocortisone was mixed with a menadione-solution in tetrahydrofurane. This suspension was then mixed in a phosphate buffer adjusted to pH 8,0. Then the bacterial suspension was added. After incubation at 30° C. under agitation, the reaction was stopped by addition of phosphoric acid. The increase in prednisolone was measured and analyzed by HPLC.

HPLC-chromatograms were obtained by a Waters-Xbrigde RP18-column using a water/acetonitrile gradient as mobile phase (chromatograms are shown in FIGS. 2-3).

Alternatively an activity assay of the production of the 20-OH-side product was realized. Prednisolone is suspended in a phosphate-buffer at pH 8.0 and incubated with bacterial suspension. After 60 min the reaction is stopped by addition of phosphoric acid. The potential increase in 20-OH ketoreduced product was then be measured by HPLC.

Truncation of NOSIM5169 permits to totally suppress the 20β-HSDH activity and thus to obtain prednisolone without 20-OH impurities (FIG. 3).

The NOSIM3735 gene was knocked out but the strains shows the same reactions as the wild-type strains, the unwanted side-reaction could not be turned off by knocking out this gene.

REFERENCE LIST

Izumikawa, M.; Murata, M.; Tachibana, K.; Ebizuka, Y. and Fujii, I. (2003): Cloning of Modular Type I Polyketide Synthase Genes from Salinomycin Producing Strain of *Streptomyces albus*. Bioorganic & Medicinal Chemistry 11: 3401-3405.

Murphy, K. C. (1998): Use of bacteriophage A recombination functions to promote gene replacement in *Escherichia coli*. J. Bacteriol. 180: 2063-2071.

Myronovskyi, M.; Welle, E.; Fedorenko, V. and Luzhetskyy, A. (2011): Glucuronidase as a Sensitive and Versatile Reporter in Actinomycetes. Applied and Environmental Microbiology, August 2011, 5370-5383.

Zhang, H.; Li, Y.; Chen, X.; Sheng, H. and An, L. (2011): Optimization of electroporation conditions for *Arthrobacter* with plasmid PART2, Journal of Microbiological Methods, 84: 114-120.

The invention claimed is:

1. A genetically modified bacterium wherein expression of a gene encoding a 20-beta-hydroxysteroid dehydrogenase (20β-HSDH) is reduced or suppressed compared to a corresponding unmodified bacterium, wherein the corresponding unmodified bacterium has Δ1-dehydrogenase activity and 20-β-hydroxysteroid dehydrogenase activity, and wherein the gene encoding a 20β-HSDH has at least 90% identity to the nucleic acid sequence set forth in SEQ ID NO: 1.

2. The genetically modified bacterium according to claim 1, wherein the gene encoding a 20β-HSDH is inactivated or deleted.

3. The genetically modified bacterium according to claim 1, wherein the gene encoding a 20β-HSDH is mutated.

4. The genetically modified bacterium according to claim 1, wherein the gene encoding a 20β-HSDH is truncated.

5. The genetically modified bacterium according to claim 1, wherein the bacterium is from the family Nocardioidaceae.

6. The genetically modified bacterium according to claim 1, wherein the genetically modified bacterium has Δ1-dehydrogenase activity, but has reduced or is devoid of 20-β-hydroxysteroid dehydrogenase activity compared to the unmodified bacterium.

7. The genetically modified bacterium according to claim 1, wherein the gene encoding a 20β-HSDH is at least 95% identical to the nucleic acid sequence set forth in SEQ ID NO: 1.

8. The genetically modified bacterium according to claim 1, wherein the gene encoding a 20β-HSDH comprises the nucleic acid sequence set forth in SEQ ID NO: 1.

9. A method for production of a genetically modified bacterium according to claim 1 comprising:
   a) providing a bacterium which has Δ1-dehydrogenase activity and 20-β-hydroxysteroid dehydrogenase activity; and b) inactivating or deleting the gene encoding a 20β-HSDH.

10. The method according to claim 9, wherein the gene encoding a 20β-HSDH comprises the nucleic acid sequence set forth in SEQ ID NO: 1.

11. A method for the production of 1,2-dehydrogenated steroid comprising:
   a) providing a steroid which is not 1,2-dehydrogenated;
   b) contacting said steroid which is not 1,2-dehydrogenated with a bacterium according to claim 1 or an extract thereof under conditions sufficient to obtain 1,2-dehydrogenated steroid.

12. The method according to claim 11, wherein the steroid which is not 1,2-dehydrogenated is a corticosteroid.

13. The method according to claim 11, wherein said steroid which is not 1,2-dehydrogenated is hydrocortisone and said method is for the production of prednisolone.

14. The method according to claim 11, wherein said method further comprises recovering and purifying said 1,2-dehydrogenated steroid.

15. The method according to claim 14, which does not comprise a step of elimination of 20 β-dehydrogenated steroid.

16. The method according to claim 11, which further comprises formulating the 1,2-dehydrogenated steroid into a pharmaceutical composition.

17. The method according to claim 11, wherein said extract has Δ1-dehydrogenase activity.

18. The method according to claim 11, wherein said extract is obtained by cell-lysis of the bacterium.

19. The method according to claim 18, wherein the cell-lysis product is fractionated in order to concentrate Δ1-dehydrogenase activity or to facilitate purification of Δ1-dehydrogenase activity.

20. The method according to claim 11, wherein the gene encoding a 20β-HSDH comprises the nucleic acid sequence set forth in SEQ ID NO: 1.

* * * * *